(12) United States Patent
O'Hagan et al.

(10) Patent No.: US 7,294,486 B2
(45) Date of Patent: Nov. 13, 2007

(54) ENZYMATIC PROCESS FOR THE SYNTHESIS OF ORGANO-FLUORINE COMPOUNDS

(75) Inventors: David O'Hagan, Fife (GB); Christoph Schaffrath, Heisberg (DE)

(73) Assignee: The University Court of the University of St. Andrews, St. Andrews (GB)

( * ) Notice: Subject to any disclaimer, the term of this patent is extended or adjusted under 35 U.S.C. 154(b) by 388 days.

(21) Appl. No.: 10/489,032

(22) PCT Filed: Sep. 5, 2002

(86) PCT No.: PCT/GB02/04032

§ 371 (c)(1),
(2), (4) Date: Nov. 10, 2004

(87) PCT Pub. No.: WO03/020945

PCT Pub. Date: Mar. 13, 2003

(65) Prior Publication Data

US 2005/0130274 A1 Jun. 16, 2005

(30) Foreign Application Priority Data

Sep. 5, 2001 (GB) .................. 0121439.4

(51) Int. Cl.
*C12P 19/38* (2006.01)
*C12N 1/20* (2006.01)
*A01N 43/04* (2006.01)
*C07H 19/00* (2006.01)
*C07H 19/173* (2006.01)

(52) U.S. Cl. ............... 435/87; 435/253.5; 435/886; 514/46; 536/27.1; 536/27.3

(58) Field of Classification Search ............ 435/87, 435/235.5, 886; 514/46; 536/27.1, 27.3
See application file for complete search history.

(56) References Cited

OTHER PUBLICATIONS

Alauddin, M.M., et al.: Evaluation of 9-'(3-F-fluoro-1-hydroxy-2-propoxy) Methyl Guanine ('F-FHPG) In Vitro and In Vivo as a Probe for PET Imaging of Gene Incorporation and Expression in Tumors. Nuclear Medicine and Biology, Elsevier Science Publishers, New York, NY, United States. vol. 26, No. 4, May, 1999, pp. 371-376.
Cherif, A., et al.: "Radiosynthesis and Biodistribution Studies of (F-18) Fluoroadenosine and (I-131)-5-Iodo-2'-0-methyl-uridine, for the Assessment of Tumor Proliferation Rate." Pharmaceutical Research, New York, vol. 12, No. 9, Suppl., 1995, p. S128.

Hamilton, J.T., et al.: "Biosynthesis of fluroacetate and 4-flurothreonine by Streptomyces Cattleya. Glycine and pyruvate and precursors." Chemical Communications, 1997, United Kingdom, vol. 2, No. 8, pp. 797-798.
Lehel, Sz., ei al.: "Synthesis of 5'-deoxy-5'-(18F) fluror-adenosine by radiofluroination of 5'-deosy-5'-haloadenosine derivatives." Journal of radioanalytical and Nuclear Chemistry, 2000 Hungary. vol. 245, No. 2, pp. 399-401.
Moss, S.J., et al.: "Fluoroacetaldehyde: A precursor of both fluoroacetate and 4-fluorothreonine in Streptomyces cattleya." Chemical Communications, Nov. 21, 2000, United Kingdom. vol. 6, No. 22, pp. 2281-2282.
O'Hagan, D., et al.: "Assay for the Enantiomeric Analysis of (2H1)-Fluroacetic Acid—Insight into the Stereochemical course of Fluroination during Flurometabolite Biosynthesis in Streptomyces Cattleya." Journal of the American Chemical Society, vol. 125, No. 2, Jan. 15, 2003, pp. 379-387.
O'Hagan, D., et al.: "Biochemistry: Biosynthesis of an organofluorine molecule." Nature, England, Mar. 21, 2002. vol. 416, No. 6878, p. 279.
Reid, K., et al.: "Biosynthesis of fluorinated secondary metabolites by Streptomyces Cattleya." Microbiology, vol. 141, No. 6, 1995, pp. 1385-1393.
Sanada, M., et al.: "Biosynthesis of Fluorothreonine and Fluoroacetic-Acid by the Thienamycin Producer Streptomyces-Cattleya." Journal of Antibiotics, Tokyo. vol. 39, No. 2, 1986, pp. 259-265.
Savarese, T.M., et al.: "5'-Deoxy-5'-Methylthioadenosine Phosphorylase 3. Role of the Enzyme in the Metabolism and Action of 5'-Halogenated Adenosine Analogs." Biochemical Pharmacology, vol. 34, No. 3, 1985, pp. 361-368.
Schaffrath, C., et al.: "Cell-free Biosynthesis of Fluoroacetate and 4-Fluorothreonine in Streptomyces Cattleya." Angewandte Chemie (International Ed. In English), Germany, Oct. 18, 2002. vol. 41, No. 20, pp. 3913-3915.
Tamura, T. , et al.: "Synthesis of fluoroacetate from Fluoride, Glycerol and Beta-Hydroxypyruvate by Streptomyces Cattleya." Journal of Bacteriology, vol. 177, No. 9, 1995, pp. 2265-2269.
Varagnolo, L., et al.: "F-labeled Radiopharmaceuticals for PET in Oncology, Excluding FDG." Nuclear Medicine and Biology, Elsevier Science and Publishers, New York, NY, United States. vol. 27, No. 2, Feb. 2000, pp. 103-112.
Zechel, D.L., et al.: "Enzymatic synthesis of Carbon-Fluorine Bonds." Journal of the American Chemical Society, United States, May 9, 2001. vol. 123, No. 18, pp. 4350-4351.

*Primary Examiner*—Herbert J. Lilling
(74) *Attorney, Agent, or Firm*—Drinker, Biddle & Reath LLP.

(57) ABSTRACT

There is described a process for the synthesis of a fluoronucleoside compound, said process comprising mixing a substrate and an enzyme from *Streptomyces cattelya* as catalyst. The process may be used to produce an $^{18}F$ labelled fluoronucleoside compound. There is also described an enzyme derived from *Streptomyces cattelya* which has the capacity to catalyse the synthesis of a fluoronucleoside compound.

11 Claims, 4 Drawing Sheets

AANSTRRPIIAFMSDLGTTDDDVAQ

Figure 4

SEQUENCE LISTING

<160> NUMBER OF SEQ ID NOS: 1

<210> SEQ ID NO 1
<211> LENGTH: 25
<212> TYPE: PRT
<213> ORGANISM: streptomyces cattleya

<400> SEQUENCE: 1

```
Ala Ala Asn Ser Thr Arg Arg Pro Ile Ile Ala Phe Met Ser Asp Leu
 1               5                  10                  15

Gly Thr Thr Asp Asp Val Ala Gln
            20                  25
```

ENZYMATIC PROCESS FOR THE SYNTHESIS OF ORGANO-FLUORINE COMPOUNDS

Figure 1:
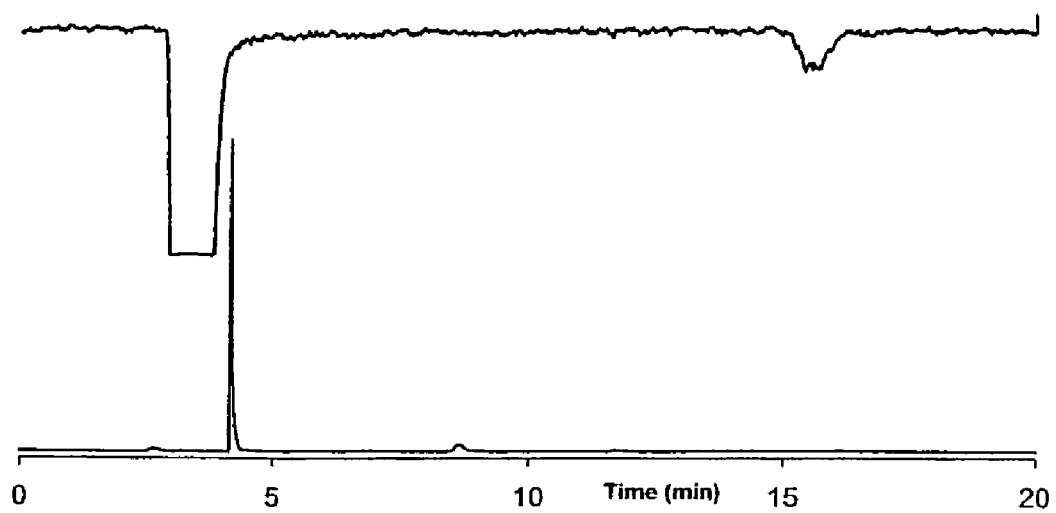

The present invention relates to a process for the enzymatic synthesis of organo-fluorine compounds, and to an enzyme having the capacity to mediate carbon-fluorine bonds.

Organo-fluorine compounds are hugely important in the fine chemicals, agrochemicals and pharmaceutical industries (blockbuster drugs include 5-fluorouracil, Prozac, meflaquin, and there are hundreds of other commercial entities) Organo-fluorine compounds also have a significant impact in the materials industry (ferromagnetic materials, Teflon etc). 6.6% of all of the compounds registered in Chemical Abstracts (there are more than 10 million) contain a fluorine atom. There is consequently a great deal of commercial interest in organo-fluorine compounds. All organo-fluorine compounds are necessarily prepared using noxious and highly toxic fluorinating reagents of anthropogenic origin. Most methods of fluorination involve toxic and environmentally incompatible processes. Additionally the chemical selectivity of processes to synthesise organo-fluorine compounds is often low. There are currently no biotechnological routes for introducing fluorine into organic compounds. To date the enzymatic synthesis of organo-fluorine compounds has been an elusive goal.

Two scientific papers (*J. Am. Chem. Soc.*, 2001, 123, 4350 and *Angew Chem. Int. Ed.*, 2001, 40, 417) recently reported the enzymatic formation of C—F bonds. These publications relate to a series of mutant glycosidase enzymes (wherein a conserved glutamate residue is replaced by various amino acids) which were able to generate glycosyl fluorides by a deviant reaction, when the enzyme was incubated with fluoride at 2M concentration. The organo-fluorine product that was generated was unstable (it was a glycosyl fluoride) and thus this process is not amenable to the synthesis of organo-fluorine compounds. The concentration of fluoride at 2 Molar is also very high indicating an inefficient process. These factors present poor prospects for commercial manufacture.

The present invention provides a process for the synthesis of a fluoronucleoside compound using a catalyst. Preferably the catalyst is an enzyme from *Streptomyces cattleya*. Preferably the enzyme is in a cell free extract, and is at least partially purified.

The fluorinase enzyme has been purified to homogeneity and partial sequence data of the N-terminus of the enzyme is also presented (see SEQ ID No. 1).

*Streptomyces cattleya* is available publicly from the culture collection held by the Agricultural Research Service Culture Collection (NRRL) in USA, under deposit No. NRRL 8057.

The present invention further provides an enzyme obtainable from *Streptomyces cattelya* characterised in that said enzyme has the capacity to catalyse the synthesis of organo-fluorine compounds, particularly fluoronucleosides. The enzyme is therefore a fluorinase enzyme. The enzyme may be usefully presented in a cell-free extract, although preferably the enzyme is at least partially purified. In some applications the enzyme is purified to homogeneity. The preferred substrate of the synthesis reaction catalysed by the enzyme is S-adenosylmethionine (SAM). Optionally SAM is generated in situ by a combination of ATP or ADP and L-methionine, in the presence of L-methionine S-adenosyl transferase. Organo-fluorine compounds produced by said enzymes include fluoroacetate and 5'-fluoro-5'-deoxyadenosine. A suitable fluoride donor substrate of the synthesis reaction is a fluoride salt, preferably a lithium, potassium or sodium fluoride salt, or is hydrogen fluoride.

The fluorinase enzyme has been purified to homogeneity. The various stages of purification are shown in the SDS Page gel of FIG. 3. The molecular weight of the fluorinase enzyme is 31.192 kd (confirmed by MALDI-TOF mass spectroscopy analysis). Non-denaturing gels indicate a molecular weight of 192 kd, suggesting that the active enzyme may be a hexamer. Edman degradation has indicated an N-terminal amino acid sequence as shown in FIG. 4.

In a further aspect, the present invention provides a fluorinase enzyme obtainable from *Streptomyces cattleya* having a molecular weight of 31 kd.

The present invention further provides the use of an enzyme described above for fluoronucleoside synthesis.

As the enzyme originates from a *Streptomyces* genus and the molecular biology of *Streptomyces* is very well developed, it is a very real prospect that in the future the gene for the enzyme could be cloned into other organisms such that the engineered organism would then have an improved capacity to generate organo-fluorine compounds.

Promotors could be inserted into the fluorinase enzyme gene within the host *Streptomyces* for similar effect.

Antibiotic biosynthesis genes from a range of *Streptomyces* sp. are currently being cloned to effect structurally modified antibiotics. There is a potential application to insert appropriate plasmids containing this gene into antibiotic gene clusters. The novel hybrid clusters may generate fluorinated antibiotics by fermentation.

A suitable fluorination enzyme substrate for the synthesis reaction is S-adenosylmethionine (SAM). In a cell-free, partially purified or purified, enzyme system SAM may be added as the substrate. However in a crude enzyme system (comprising ruptured cells from which cell debris has been removed, suitably by centrifugation), ATP or ADP and L-methionine are sufficient to promote the fluorination. SAM may be synthesised in situ from ATP by the action of L-methionine S-adenosyltransferase. ADP disproportionate to AMP and ATP, followed by the resultant conversion of ATP to SAM. The crude enzyme system has sufficient L-methionine S-adenosyltransferase present to catalyse the process.

One suitable substrate is a fluoride salt, preferably a lithium, potassium or sodium fluoride salt. Hydrogen fluoride is also suitable as a substrate. The concentration of the fluoride ions is preferably 2 to 10 mM, although higher or lower concentrations of fluoride ions are also possible. Indeed significantly higher concentrations of fluoride ions may be of utility in certain commercial processes.

The organo-fluorine compound produced may be 5'-fluoro-5'-deoxyadenosine (5'-FDA). The 5'-fluoro-5'-deoxyadenosine may be used as an intermediate and in the production of other organo-fluorines, for example the organo-fluorine compound fluoroacetate. In this case the crude enzyme system will comprise additional enzymes, and will catalyse the conversion of 5'-fluoro-5'-deoxyadenosine to fluoroacetate as shown in Scheme 1.

Scheme 1

SAM + inorganic fluoride $\xrightarrow[\text{protein extract}]{S.\ cattleya}$

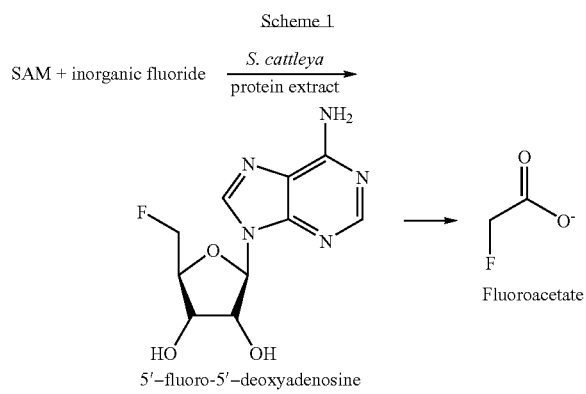

5'-fluoro-5'-deoxyadenosine

We have found that the more purified the enzyme system is, the greater the accumulation of 5'-fluoro-5'-deoxyadenosine as the biotransformation product.

The present invention further provides a coupled enzyme biotransformation process utilising the enzymes, L-methionine S-adenosyltransferase and the fluorination enzyme as catalysts and wherein L-methionine, ATP and fluoride are added as substrates.

A cell-free extract from the bacterium Streptomyces cattleya has the ability to generate 5'-fluoro-5'-deoxyadenosine by the combination of inorganic fluoride with ATP and L-methionine, or more preferably by the combination of inorganic fluoride with S-adenosylmethionine, the co-factor generated by a combination of ATP and the amino acid L-methionine as shown in Scheme 2.

Scheme 2

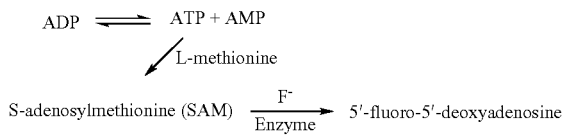

A crude extract from the bacterium Streptomyces cattleya will convert the 5'-fluoro-5'-deoxyadenosine to fluoroacetate. A partially purified cell-free extract produces 5'-fluoro-5'-deoxyadenosine.

The process of the present invention generates a stable compound, containing a fluoromethyl group.

Nucleosides and their derivatives are widely used in DNA/RNA chemistry and as antiviral compounds. 5'-fluoro-5'-deoxyadenosine has application in a diverse range of potential applications in such research.

Preferably the organo-fluorine compound may be labelled with $^{18}F$ for positron emission tomography (PET). Preferably the source of $^{18}F$ from the synchrotron is potassium fluoride, and preferably this is the same source of fluoride used by the enzyme. Hydrogen fluoride may also be used and other fluoride salts are likewise possible. The half-life of $^{18}F$ is 110 minutes, and so rapid synthesis routes will be a considerable advantage.

Fluorinated sugar (e.g. a fluoronucleoside compound) generated according to the present invention comprising $^{18}F$ may be injected into a patient, and the patient may then be imaged.

Fluoroacetate has been used to study glial metabolism in the brain of a rat and central nervous system of the rat. The invention provides a suitable route for the synthesis of $^{18}F$-fluoroacetate for positron emission tomography (PET) studies. This process introduces the fluorine enzymatically rather than chemically. The use of $^{18}F$-fluoroacetate synthesised as described above for PET studies is thus part of the present invention.

[$^{18}F$]-5'-fluoro-5'-deoxyadenosine may be used to explore the nucleic acid accumulation in tumour tissue.

PET offers the highest spatial and temporal resolution of all nuclear medicine imaging modalities and can allow quantitation of tracer concentrations in tissues. The use of $^{18}F$ offers a number of advantages over $^{11}C$ as a PET radionuclide, primarily because of its longer half-life (110 minutes for $^{18}F$ versus 20 minutes for $^{11}C$). From a radiochemistry and radiopharmacy perspective, $^{18}F$-labelled pharmaceuticals allows substantially more time for radiochemical synthesis, purification and quality control of doses for use in vivo experiments.

$^{18}F$-labelled radiopharmaceuticals can be synthesised according to the process of the present invention in quantities sufficient for the formulation of multiple doses from a single production and for remote distribution to locations without on-site cyclotron facilities. Aliphatic $^{18}F$ labelled compounds are commonly produced by nucleophilic substitution with [$^{18}F$]$F^-$ for a nucleofuge (i.e. halogens, sulfonates, cyclic sulfamidates) in a polar aprotic solvent (i.e. acetonitrile, dimethylsufoxide) and therefore only a limited set of synthetic methods are available for rapid radiofluorination. The radiolabelling of [$^{18}F$]-5'-fluoro-5'-deoxyadenosine by nucleophilic substitution using 5'-halogenated adenosine derivatives as precursor fails to produce the desired product with good yield (Lethel Sz., Horváth G., Boros I., Mikecz P., Trón L. Journal of Radioanalytical and Nuclear Chemistry, vol 245, No 2 (2000) 399-401). The method of the present invention provides a means of radiolabelling PET isotopes leading to novel radiopharmaceuticals or improved availability of existing tracers.

The process of the present invention provides a process for enzymatically synthesising radiolabelled [$^{18}F$]-5'-fluoro-5'-deoxyadenosine ([$^{18}F$]-5'-FDA) for PET.

It is a very real prospect that the biosynthesis of 5'-fluoro-5'-deoxyadenosine by the present invention will enable a novel preparation of 5-fluoro-5-deoxyribose by either further chemical or enzymatic treatment of the enzymatic product 5'-fluoro-5'-deoxyadenosine, such that the adenine base is hydrolytically cleaved.

The invention will now be described by way of example only, with respect to the figures in which:

FIG. 1—shows a HPLC chromatogram of reaction mixture aliquots; 5 to 20% MeCN in 50 mM $KH_2PO_4$; flow 1 ml/min.

Figure 2:
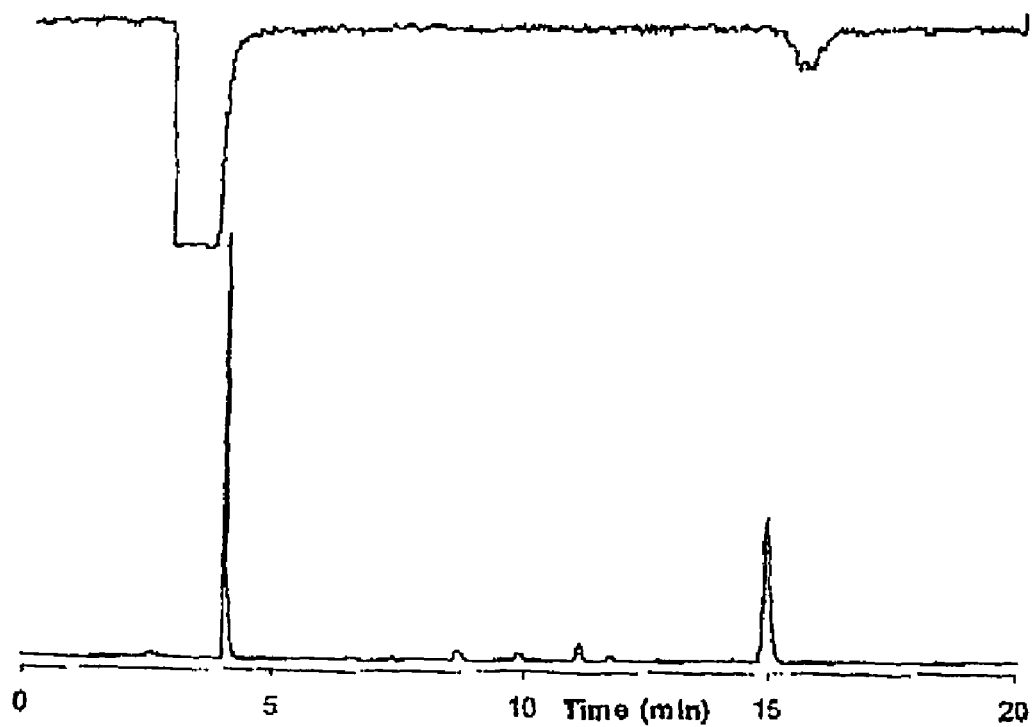

FIG. 2—shows a HPLC chromatogram of [$^{18}F$]5'-FDA co-injected with standard 5'-FDA C18 column; 5 to 20% MeCN in 50 mM $KH_2PO_4$; flow 1 ml/min.

Figure 3:
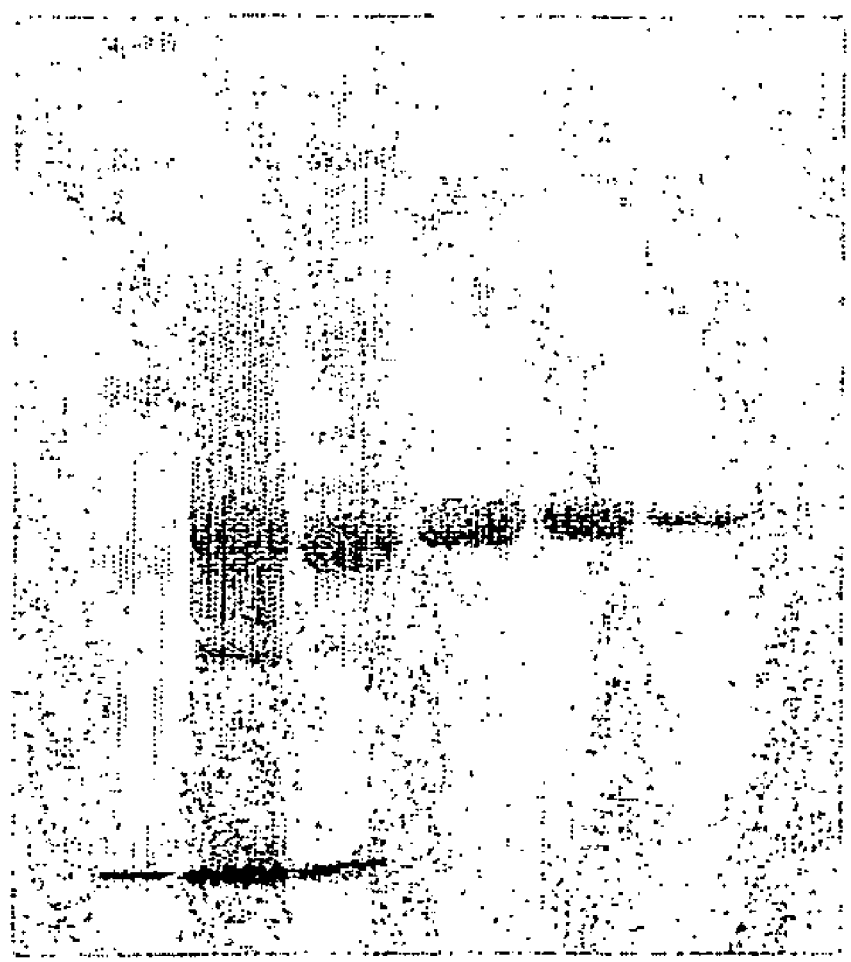

FIG. 3—shows the purification protocol for the fluorine enzyme wherein Lane 1 shows molecular weight markers, Lane 2 shows crude cell free extract, Lane 3 shows 45-60% $(NH_4)_2SO_4$ cut, Lane 4 shows phenyl sepharose column, Lane 5 shows gel filtration superdex 200, Lane 6 shows anion exchange Source 15 Q. The Lanes are numbered from left to right.

FIG. 4—shows the N-terminal 25 amino acid sequence of the fluorinase enzyme.

EXAMPLE 1

Experimental Procedures

Materials and Culture Conditions

Cells of S. cattleya (NRRL 8057) were grown under conditions as described in K. A. Reid, J. T. G. Hamilton, R. D. Bowden, D. O'Hagan, L. Dasaradhi, M. R. Amin and D. B. Harper, Microbiol., 1995, 141, 1385. After 7 days of incubation the cells were harvested by centrifugation (9000 rpm, 25 min), washed three times with Tris buffer (100 mM, pH 7.8) and stored at −20° C. until required. ATP was purchased from Fluka, other biochemicals were purchased from Sigma. Sonication was carried out with a vibra cell (Sonic & Materials), $^{19}$F and $^1$H-NMR were recorded on a Varian Inova NMR spectrometer. Enzyme purification was performed with an AKTA Prime System (Pharmacia). For Analytical and semipreparative HPLC a Varian System was used, containing a pump (9012, Varian) and variable wavelength UV detector (9050, Varian).

Enzylmatic Preparation of 5-fluoroadenosine in a Cell Free Extract of Streptomyces cattleya A cell-free extract of S. cattleya was prepared from frozen cells which were resuspended in Tris-buffer (100 nM, pH 7.8) containing potassium bicarbonate (200 mM) (0.2 g wt cells weight/ml). The cell suspension was sonicated (three pulses of 30 sec duration at 40-50% microtip power) and the cell debris was removed by centrifugation (20,000 rpm, 20 min). To supernatant (900 μl) was added ATP (5 mM), $MgCl_2$ (15 nM), L-methionine (0.2 mM), potassium fluoride (10 mM) in a total volume of 1 ml and incubated for 16 hours at 26° C. in a water bath. $^{19}$F-NMR analysis demonstrate the formation of an organofluorine compound $\delta_F$ (470.445 MHz; $^2H_2O$)-229.65 (J 47.5, 30.1). Incubation of cell-free extract (970 μl) supplemented with SAM (0.4 mM) and potassium fluoride (10 mM) for 16 hours at 26° C. also resulted in the formation of 5'-fluoro-5'-deoxyadenosine.

Preparation of 5'-fluoro-5'-deoxyadenosine Using a Purified Protein Extract from Streptomyces cattleya A cell-free extract from S. cattleya cells was prepared as described above. Ammonium sulfate was added to the cell-free extract and the precipitate at 45-60% saturation was kept. The precipitate was resuspended in Tris-buffer (100 mM, pH 7.8) containing potassium bicarbonate (200 mM) and desalted using a HiTrap desalting column (5 ml bed volume, Pharmacia). The protein was then applied to an anion exchange column (HiTrap QXL, 1 ml bedvolume, Pharmacia) previously equilibrated with the same buffer. The column was washed with 20 ml of buffer followed by 20 ml of Tris-buffer (100 mM, pH 7.8) containing potassium bicarbonate (200 mM) and KCl (1 M). The collected fractions were assayed by incubating a small volume (900 μl, 970 μl) with either ATP (5 mM), $MgCl_2$ (15 mM), L-methionine (0.2 mM), potassium fluoride (10 mM) or with SAM (0.4 mM) and potassium fluoride (10 mM) for 16 hours at 26° C. Only in the presence of SAM and fluoride was formation of 5'-fluoro-5'-deoxyadenosine observed.

Purification of 5'-fluoro-5'-deoxyadenosine

For purification of the organofluorine product, a cell-free extract (15 ml) was prepared as described before and incubated with ATP (5 mM), $MgCl_2$ (15 mM), L-methionine (0.2 mM), potassium fluoride (10 mM) for one day at 26° C. After that time the biotransformation mixture was heated at 90° C. for 10 minutes and denatured protein was removed by centrifugation. The supernatant was lyophilised the resultant powder was dissolved in $H_2O$ (2 ml) and remaining solids were removed by centrifugation. The clear supernatant (100 μL) was applied to a Hypersil 5 μm C-18 column (250×10 mm, Phenomenex) and eluted isocratically (potassium phosphate buffer (50 mM)/acetonitrile, 95.5) at a flow rate of 5 ml/min. Detection was by UV at 260 nm.

Fractions corresponding to observed peaks were collected and analysed by $^{19}$F-NMR. Fractions containing the fluorinated product were combined, lyophilised and dimethyl-$d_6$ sulfoxide (1.5 ml) was added. The solids were removed by centrifugation and the clear supernatant was used for structure elucidation by $^1$H and $^{19}$F-NMR. $\delta_H$ (500 MHz; DMSO) 4.11 (2×m, $J_{FH}$ 21.4, 1H, 4'-H), 4.20 (t, J5.0, 1H, 3'-H), 4.49 (t, J5.0, 1H, 4'-H), 4.62 (2×m, $J_{FH}$ 47.8, 2H, 5'-H), 5.90 (t, J5.0, 1H, 1'-H), 8.06 (s, 1H, 2-H), 8.20 (s, 1H, 8-H); $\delta_F$ (470.553 MHz; DMSO)-229.69 (J 48.9, 30.1).

EXAMPLE 2

The partially purified fluorinase enzyme (0.4 mg/ml protein) was incubated with [$^{18}$F]HF (in solution in [$^{18}$O]$H_2O$) and SAM (0.4 mM) at 23° C. at pH=7.0. The aliquots collected at different time points were passed through an anion exchange column and injected into a high-pressure liquid chromatography (HPLC) system coupled to a radioactivity detector to follow the course of the radiolabelling.

Analysis of the aliquots by radio-HPLC showed two radioactive peaks. The retention time of the first radioactive signal eluting at 3.6 minutes on the reverse-phase column (corresponding to the dead volume of the column) is consistent with unreacted [$^{18}$F]fluoride or polar products such as [$^{18}$F]fluorine bound to proteins. The only radioactive non-polar peak was detected at 15.6 minutes (FIG. 1). When aliquots were co-injected with an authentic sample of 5'-FDA, the UV signal of the reference compounds co-eluted with the radioactive peak eluting at 15.6 minutes (FIG. 2). The apparent difference in the retention times (approximately 0.5 minutes) is an artefact to physical separation of the radioactivity and UV detectors (FIGS. 1 and 2).

In conclusion, an enzymatic radiolabelling method for the production of [$^{18}$F]-5'-FDA has been successfully developed starting from SAM and [$^{18}$F]HF.

The invention claimed is:

1. A process for the synthesis of a fluoronucleoside compound, said process comprising mixing a substrate, a fluoride compound and an enzyme comprising an amino acid sequence SEQ ID NO:1 as a catalyst, said enzyme obtainable from *Streptomyces cattleya*.

2. A process as claimed in claim 1 wherein the enzyme is at least partially purified.

3. A process as claimed in claim 1 wherein the substrate comprises S-adenosylmethionine.

4. A process as claimed in claim 1 wherein said fluoronucleoside compound is synthesised by mixing a fluoride salt with a crude enzyme system from *Streptomyces cattleya* comprising ATP and L-methionine or ADP and L-methionine together with L-methionine S-adenosyltransferase.

5. A process as claimed in claim 1 wherein the fluoride compound is a lithium, potassium or sodium fluoride salt.

6. A process as claimed in claim 1 wherein said fluoride compound is hydrogen fluoride.

7. A process as claimed in either claim 5 wherein the concentration of fluoride ions is 2 to 10 mM.

8. A process as claimed in claim 1 wherein the fluoronucleoside compound is 5'-fluoro-5'-deoxyadenosine.

9. A process as claimed in claim 1 wherein the fluoride compound is labelled with $^{18}$F.

10. A process as claimed in claim 9 wherein the fluoronucleoside compound is labelled with $^{18}$F.

11. A process as claimed in claim 1 wherein the enzyme is obtained from *Streptomyces cattleya*.

* * * * *